(12) United States Patent
Bahammam

(10) Patent No.: US 11,793,754 B1
(45) Date of Patent: Oct. 24, 2023

(54) SODIUM HYPOCHLORITE AND CHLORHEXIDINE BASED NANOEMULSIONS AND A METHOD OF PREPARATION THEREOF

(71) Applicant: King Abdulaziz University, Jeddah (SA)

(72) Inventor: Laila Ahmed Salim Bahammam, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/842,339

(22) Filed: Jun. 16, 2022

(51) Int. Cl.
| | |
|---|---|
| *A61K 9/107* | (2006.01) |
| *A61K 33/20* | (2006.01) |
| *A61K 47/26* | (2006.01) |
| *A61K 47/12* | (2006.01) |
| *A61K 31/155* | (2006.01) |
| *B82Y 5/00* | (2011.01) |

(52) U.S. Cl.
CPC .......... *A61K 9/1075* (2013.01); *A61K 31/155* (2013.01); *A61K 33/20* (2013.01); *A61K 47/12* (2013.01); *A61K 47/26* (2013.01); *B82Y 5/00* (2013.01)

(58) Field of Classification Search
CPC .... A61K 9/1075; A61K 31/155; A61K 33/20; A61K 47/12; A61K 47/26; B82Y 5/00
See application file for complete search history.

(56) References Cited

U.S. PATENT DOCUMENTS

| | | | | |
|---|---|---|---|---|
| 2002/0119207 | A1* | 8/2002 | Baker, Jr. | A61P 17/10 424/769 |
| 2020/0022386 | A1* | 1/2020 | Schwarz | A61K 9/0095 |
| 2020/0188237 | A1 | 6/2020 | Feldman | |

FOREIGN PATENT DOCUMENTS

| | | |
|---|---|---|
| CN | 112057626 A | 12/2020 |
| EP | 2 491 915 B1 | 7/2019 |
| IL | 170738 B | 12/2010 |
| KR | 10-1941420 | 1/2019 |

OTHER PUBLICATIONS

Abdelmonem et al. ("Formulation and characterization of chlorhexidine HCl nanoemulsion as a promising antibacterial root canal irrigant: in-vitro and ex-vivo studies", Int J Nanomedicine. 2019; 14: 4697-4708.) (Year: 2019).*
Marina (RU2731904C1 Machine English Translation) (Year: 2019).*
Dabhi, et al. ; Preparation and In Vivo Evaluation of Self-Nanoemulsifying Drug Delivery System (SNEDDS) Containing Ezetimibe ; Current Nanoscience, vol. 7, Issue 4 ; pp. 616-627 ; Abstract Only ; 2 Pages.
Jeong, et al. ; Assessment of the cytotoxic effects and chemical composition of the insoluble precipitate formed from sodium hypochlorite and chlorhexidine gluconate ; International Endodontic Journal ; Jun. 1, 2021 ; 10 Pages.

* cited by examiner

*Primary Examiner* — Robert A Wax
*Assistant Examiner* — Quanglong N Truong
(74) *Attorney, Agent, or Firm* — Oblon, McClelland, Maier & Neustadt, L.L.P.

(57) ABSTRACT

A nanoemulsion, and a method of preparing the nanoemulsion is disclosed. The nanoemulsion includes sodium hypochlorite (NaOCl), chlorhexidine (CHX), and a self-nanoemulsifying delivery system (SNEDS) which further includes at least one oil, at least one surfactant, and at least one co-surfactant, wherein no parachloroaniline is present in the nanoemulsion after 1 hour at room temperature.

13 Claims, 3 Drawing Sheets

SODIUM HYPOCHLORITE AND CHLORHEXIDINE BASED NANOEMULSIONS AND A METHOD OF PREPARATION THEREOF

BACKGROUND

Technical Field

The present disclosure is directed to nanoemulsions, particularly to sodium hypochlorite and chlorhexidine based nanoemulsions and a method of making thereof.

Description of Related Art

The "background" description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present invention.

A leading cause of pulp necrosis and periapical bone destruction is a bacterial infection. Therefore, the main goal of a root canal treatment is to eliminate or lower the bacterial infection via thorough cleaning and a shaping procedure. Although chemo-mechanical preparation reduces the bacterial number, they cannot be removed entirely. Conventionally, sodium hypochlorite (NaOCl) is considered a gold-standard irrigant due to its broad-spectrum antibacterial activity and tissue-dissolving capability. However, the tissue dissolving ability with NaOCl is effective only at high concentrations. Another drawback of NaOCl is its inability to remove the smear layer and lack of prolonged antimicrobial activity. Chlorhexidine (CHX), an alternative to NaOCl, has antibacterial efficacy comparable to NaOCl, but lacks the ability to dissolve tissue. In recent years, CHX is used in combination with NaOCl to maximize the antibacterial activity and get advantages of optimal features of both chemicals. However, the presence of NaOCl in the canals during irrigation with CHX produces an orange-brown precipitate known as parachloroaniline (PCA) which causes dentin staining. In addition to causing dentin staining, the precipitate occludes the dentinal tubules and may compromise the seal of the obturated root canal. Leaching of PCA from the insoluble precipitate is also of concern for its carcinogenic and cytotoxic property. Therefore, there exists a need to develop a formulation that can overcome the limitations of the art.

SUMMARY

In an exemplary embodiment, a nanoemulsion is described. The nanoemulsion includes sodium hypochlorite (NaOCl), chlorhexidine (CHX), and a self-nanoemulsifying delivery system (SNEDS). The SNEDS includes at least one oil, at least one surfactant, and at least one co-surfactant. The nanoemulsion has no parachloroaniline present after 1 hour at room temperature.

In some embodiments, the SNEDS include 5-20 weight percent (wt. %) of the oil, 40-60 wt. % of the surfactant, and 30-50 wt. % of the co-surfactant, based on the total weight of the oil, the surfactant, and the co-surfactant.

In some embodiments, the nanoemulsion includes 40-60 volume percent (v. %) SNEDS, 20-30 v. % of NaOCl, and 20-30 v. % of CHX, based on the total volume of the SNEDS, the NaOCl, and the CHX.

In some embodiments, the NaOCl is a solution of 1-20% NaOCl in water.

In some embodiments, the CHX is a solution of 1-15% CHX in water.

In some embodiments, the oil is at least one selected from the group including one or more of isopropyl myristate, olive oil, sunflower oil, soyabean oil, safflower oil, coconut oil, ethyl oleate, oleic acid, glyceryl dicaprate, glycerol caprylate caprate, and glyceryl monocaprylate.

In some embodiments, the surfactant is at least one selected from the group including one or more of polyoxyethylene (20) sorbitan monooleate, polyethoxylated castor oil, polyoxyethylene (20) sorbitan monolaurate, poloxamer 188, and lauroyl polyoxyl-32 glyceride.

In some embodiments, the co-surfactant is at least one selected from the group including oleoyl polyoxyl-6 glycerides, polyglyceryl-3 dioleate, ethanol, polyethylene glycol (PEG) 200, carbitol, and ethylene glycol.

In some embodiments, the oil is oleic acid.

In some embodiments, the surfactant is polyoxyethylene (20) sorbitan monooleate.

In some embodiments, the co-surfactant is PEG 200.

In some embodiments, the nanoemulsion has a globule size less than 200 nm.

In some embodiments, the nanoemulsion has a zeta potential of −70 to −40 mV.

In some embodiments, the CHX is dispersed within a first group of SNEDS particles, the NaOCl is dispersed within a second group of SNEDS particles, and the NaOCl and the CHX do not have physical contact.

In some embodiments, at least 95% of human cells are viable after exposure to the nanoemulsion.

In an exemplary embodiment, a method of making the nanoemulsion is described. The method includes mixing the oil, the surfactant, and the co-surfactant to form a mixture. The method further includes combining the mixture with NaOCl or CHX to form a NaOCl nanoemulsion solution or a CHX nanoemulsion solution, respectively. Furthermore, the method includes vortexing the solutions for at least 10 seconds, and further combining the NaOCl nanoemulsion solution and the CHX nanoemulsion solution and vortexing for at least 2 minutes to form the nanoemulsion.

In some embodiments, the nanoemulsion is an irrigant formulation for reducing a bacterial proliferation in a root canal of a patient. The reduction of the bacterial proliferation is compared to a bacterial proliferation of the otherwise same root canal when treated in the otherwise same manner except without administering the nanoemulsion or derivative thereof. In some embodiments, the reduction of the bacterial proliferation is compared to a bacterial proliferation of the otherwise same root canal when treated with NaOCl or CHX with no SNEDS present.

In an exemplary embodiment, a method of irrigating the root canal during an endodontic procedure is described. The method includes providing access to the root canal of a tooth, and further introducing the nanoemulsion to the root canal.

The foregoing general description of the illustrative embodiments and the following detailed description thereof are merely exemplary aspects of the teachings of this disclosure and are not restrictive.

BRIEF DESCRIPTION OF DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
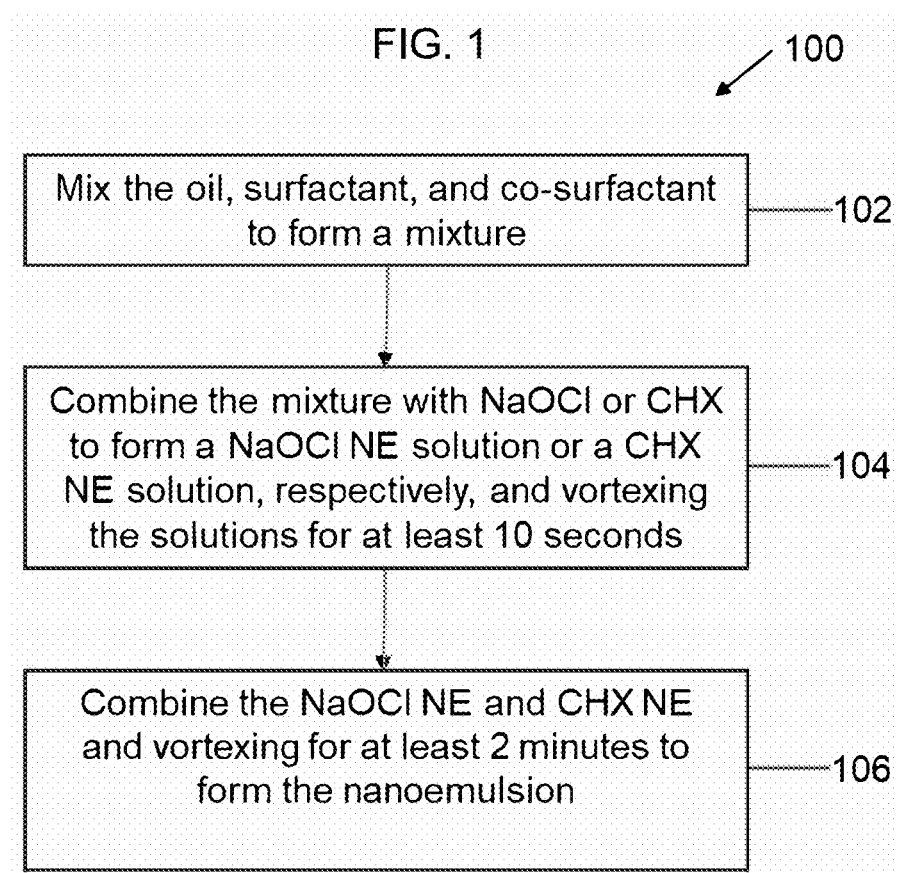
FIG. 1 is a flowchart of a method of making the nanoemulsion, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

The term "nanoemulsion" refers to nano-sized emulsions in which two immiscible liquids are mixed to form a single phase by means of an emulsifying agent, i.e., surfactant and co-surfactant.

Embodiments of the present disclosure are directed towards a self-nano emulsifying system, including a combination of sodium hypochlorite (NaOCl) and chlorhexidine (CHX), in some cases referred to as the nanoemulsion. The nanoemulsion of the present disclosure prevents or minimizes precipitation by avoiding or minimizing the chance for the two irrigants (NaOCl and CHX) to contact each other, thereby overcoming the drawbacks associated with precipitation. The resulting nanoemulsion was characterized for parachloroaniline (PCA), tissue dissolving ability, and biocompatibility studies, and the results were further compared to liquid solutions of NaOCl and CHX irrigants. The nanoemulsion of the present disclosure was substantially free of PCA. Experimental results indicate that the nanoemulsion demonstrates better tissue dissolving ability and antibacterial activity than the conventionally used irrigants. Although, aspects of the present disclosure are related to using the nanoemulsion in a root canal, it may be understood by a person skilled in the art that aspects of the present disclosure may be directed towards other endodontic procedures, as well.

In an aspect of the present disclosure, a nanoemulsion is described. The nanoemulsion includes NaOCl, CHX, and a self-nanoemulsifying delivery system (SNEDS) which further includes at least one oil, at least one surfactant, and at least one co-surfactant. In an embodiment, the SNEDS include 5-20 weight percent (wt. %), preferably 7-18 wt. %, or 10-15 wt. % of the oil, 40-60 wt. %, preferably 45-55 wt. %, or 47-52 wt. % of the surfactant, and 30-50 wt. %, preferably 35-45 wt. %, or 38-42 wt. % of the cosurfactant, based on the total weight of the oil, the surfactant, and the co-surfactant. In some embodiments, the oil is at least one selected from the group including isopropyl myristate, olive oil, sunflower oil, soyabean oil, safflower oil, coconut oil, ethyl oleate, oleic acid, glyceryl dicaprate, glycerol caprylate caprate, and glyceryl monocaprylate. In a preferred embodiment, the oil is oleic acid. In some embodiments, the surfactant is at least one selected from the group including polyoxyethylene (20) sorbitan monooleate, polyethoxylated castor oil, polyoxyethylene (20) sorbitan monolaurate, poloxamer 188, and lauroyl polyoxyl-32 glyceride. In a preferred embodiment, the surfactant is polyoxyethylene (20) sorbitan monooleate. In some embodiments, the co-surfactant is at least one selected from the group consisting of oleoyl polyoxyl-6 glycerides, polyglyceryl-3 dioleate, ethanol, polyethylene glycol (PEG) 200, carbitol, and ethylene glycol. In a preferred embodiment, the co-surfactant is PEG 200.

The nanoemulsion further includes NaOCl, and CHX, where less than 50 parts per million (ppm), preferably less than 30 ppm, 20 ppm, or 10 ppm of parachloroaniline is present in the nanoemulsion after 1 hour, preferably 24 hours, or 1 week at room temperature preferably up to 50° C. In a preferable embodiment, no parachloroaniline is present in the nanoemulsion after 1 hour at 25° C.

In some embodiments, the nanoemulsion includes 40-60 v. % SNEDS, preferably 45-55 v. %, or 48-52 v. %, 20-30 v. % of NaOCl, preferably 22-28 v. %, or 24-26 v. %, and 20-30 v. % of CHX, preferably 22-28 v. %, or 24-26 v. %, based on the total volume of the SNEDS, the NaOCl, and the CHX. In some embodiments, the concentration of the NaOCl in an initial solution (prior to adding to the nanoemulsion) is 1-20%, preferably 1-10%, or 1-5% NaOCl in water. In some embodiments, the concentration of the CHX in an initial solution (prior to adding to the nanoemulsion) is 1-15%, preferably 1-10%, or 1-5% CHX in water.

The NaOCl and CHX are positioned such that the CHX is dispersed within a first group of SNEDS particles, and the NaOCl is dispersed within a second group of SNEDS particles, which minimizes contact between both the irrigants, thereby circumventing the drawbacks associated with precipitation. In an embodiment, the oil, surfactant, and co-surfactant particles form a layer around, and at least partially enclose the NaOCl or CHX separately. Therefore, in the nanoemulsion the CHX and NaOCl are each surrounded by the SNEDS particles and do not physically come into contact with each other.

In some embodiments, the nanoemulsion of the present disclosure has a globule size of less than 200 nanometers (nm), preferably 100-200 nm, or 130-160 nm. The nanoemulsion has a zeta potential of −70 to −40 millivolt (mV), preferably −70 to −50 mV, or −70 to −60 mV. This high value indicates a high degree of repulsion between the two irrigants, and consequently greater stability. A low zeta-potential value is indicative of coagulation between the two irrigants, which can cause precipitation, and consequently dentin staining. Further, unlike some of the conventionally used irrigants which are toxic to human cells, the nanoemulsion of the present disclosure demonstrates at least 95%, preferably 98% or 100% of cell viability in human cells after exposure to the nanoemulsion.

In an aspect of the present disclosure, the nanoemulsion is an irrigant formulation for reducing a bacterial proliferation in a root canal of a patient. In an embodiment, the reduction of the bacterial proliferation is compared to a bacterial proliferation of the otherwise same root canal when treated in the otherwise same manner except without administering the nanoemulsion or derivative thereof. In another embodiment, the reduction of the bacterial proliferation is compared to a bacterial proliferation of the otherwise same root canal when treated with NaOCl or CHX with no SNEDS present.

In another aspect of the present disclosure, a method of irrigating a root canal during an endodontic procedure is described. The method includes providing access to the root canal of a tooth, and further introducing the nanoemulsion to the root canal. In some embodiments, the method for irrigating is effective for a variety of prepared tooth surfaces. The surface can be a surface that is an endodontic situs, a surface that is an instrumented root canal, a surface prepared for a periodontic procedure, a surface that is prepared site for tooth restoration, a surface prepared for tooth reconstruction, or any surface of a surgical site whether it is a bone or a soft tissue.

In an embodiment, the nanoemulsion further comprises at least one analgesic. The analgesic further provides a numbing or soothing feeling when applied to the oral cavity during a dental procedure. In an embodiment, the analgesic is selected from the group consisting of lidocaine, articaine, tetracaine, benzocaine, and prilocaine. In a preferred embodiment, the analgesic is lidocaine. In an embodiment, the nanoemulsion includes 40-60 v. % SNEDS, preferably 45-55 v. %, or 48-52 v. %, 20-30 v. % of NaOCl, preferably 22-28 v. %, or 24-26 v. %, 20-30 v. % of CHX, preferably 22-28 v. %, or 24-26 v. %, and 1-10 v. % analgesic, based on the total volume of the SNEDS, the NaOCl, the CHX, and the analgesic. In some embodiments, the analgesic is a solution of 1-15%, preferably 1-10%, or 1-5% analgesic in water. In an embodiment, the NaOCl, CHX, and analgesic are positioned such that the CHX is dispersed within a first group of SNEDS particles, the NaOCl is dispersed within a second group of SNEDS particles, and the analgesic is dispersed in a third group of SNEDS particles. In a preferable embodiment, the analgesic is dispersed in particles of a low melting wax or a wax having a low softening temperature, prior to incorporation into the nanoemulsion. Examples of preferable waxes include paraffin wax, soy wax, and wax blends. Wherein the wax blends contain a 1:5 to 5:1 weight ratio, preferably 1:2 to 2:1 weight ratio, of at least one of a paraffin wax and a soy wax blended with a low molecular weight polyolefin wax such as polyethylene wax having a $M_n$ molecular weight of 250-1,000 or 500-750 Daltons. Such blends provide a desirable combination of low melting/softening temperatures and low hardness permitting their use for controlled and gentle release of analgesic in the oral cavity upon impingement of tissue surfaces. In an embodiment, 1-20 wt. % of the analgesic dispersed in the wax is added to the nanoemulsion, based on the total weight of the analgesic dispersed in the wax, and the nanoemulsion.

Referring to FIG. 1, a flow chart of a method 100 of making the nanoemulsion is illustrated. The order in which the method 100 is described is not intended to be construed as a limitation, and any number of the described method steps can be combined in any order to implement the method 100. Additionally, individual steps may be removed or skipped from the method 100 without departing from the spirit and scope of the present disclosure.

At step 102, the method 100 includes mixing the oil, surfactant, and cosurfactant to form a mixture. In some embodiments, the oil is at least one selected from the group consisting of isopropyl myristate, olive oil, sunflower oil, soyabean oil, safflower oil, coconut oil, ethyl oleate, oleic acid, glyceryl dicaprate, glycerol caprylate caprate, and glyceryl monocaprylate. In a preferred embodiment is oleic acid. In some embodiments, the surfactant is at least one selected from the group consisting of polyoxyethylene (20) sorbitan monooleate, polyethoxylated castor oil, polyoxyethylene (20) sorbitan monolaurate, poloxamer 188, and lauroyl polyoxyl-32 glyceride. In a preferred embodiment, the surfactant is polyoxyethylene (20) sorbitan monooleate. In some embodiments, the co-surfactant is at least one selected from the group consisting of oleoyl polyoxyl-6 glycerides, polyglyceryl-3 dioleate, ethanol, polyethylene glycol (PEG) 200, carbitol, and ethylene glycol. In a preferred embodiment, the co-surfactant is PEG 200.

At step 104, the method 100 includes combining the mixture with NaOCl or CHX to form a NaOCl nanoemulsion (NE) solution or a CHX nanoemulsion (NE) solution, respectively, and vortexing the solutions for at least 10 seconds, preferably 10-30 s, or 10-20 s. In some embodiments, the vortexing is to obtain a homogeneous phase system. In some embodiments, the NaOCl is a solution of 1-20%, preferably 1-10%, or 1-5% NaOCl in water. In some embodiments, the CHX is a solution of 1-15%, preferably 1-10%, or 1-5% CHX in water. In a preferred embodiment, about 5.25% NaOCl, or 2% CHX was used prepare the NaOCl nanoemulsion solution, and CHX nanoemulsion solution.

At step 106, the method 100 includes combining the NaOCl nanoemulsion solution and CHX nanoemulsion solution and vortexing for at least 2 minutes, preferably 2-5 mins, or 2.5-3 mins to form the nanoemulsion. In a preferred embodiment, the NaOCl and CHX solutions were vortexed at 35 Hz for 3 minutes to obtain a single homogenous phase of the CHX—NaOCl nanoemulsion. In an embodiment, the NaOCl nanoemulsion solution and CHX nanoemulsion solution are combined to form a new nanoemulsion solution including both irrigants.

EXAMPLES

The following examples describe and demonstrate exemplary embodiments of the nanoemulsion as described herein. The examples are provided solely for the purpose of illustration and are not to be construed as limitations of the present disclosure, as many variations thereof are possible without departing from the spirit and scope of the present disclosure.

Example 1: Self-Nanoemulsifying Delivery System (SNEDS) Preparation

Mixture design by a special cubic model was utilized to prepare chlorhexidine/sodium hypochlorite loaded-SNEDS with minimum globule size and maximum physical stability represented in the zeta potential. A number of 10 formulations were suggested using the statistical package Statgraphics Centurion XVIII Software (StatPoint, Inc., Herndon, VA). Each formula contains different percentages of the oil, surfactant, and co-surfactant to get a total of 100% three component system. Oleic acid was used as the oil component in range of 10-15%, Tween 80 (polyoxyethylene (20) sorbitan monooleate) as the surfactant in range of 45-50%, while polyethylene glycol (PEG 200) as the co-surfactant in range of 35-40%. The design was run in a single block with a fully randomized order, as illustrated in (Table 1), to provide protection against the effect of lurking variables.

Each SNEDS mixture was prepared using the specified amount of each component in a screw cap vial and mixed well. After preparing 10 formulations using of SNEDS according to (Table 1), 1 mL of each formula is mixed with either 5.25% NaOCl (1 mL), or 2% CHX (1 ml) to prepare 1:1 NaOCl-SNEDS, and 1:1 CHX-SNEDS and vortexed using (Zx3 Vortex shaker-VELP Scientifica) for 15 seconds to insure mixing and to obtain a homogenous phase system. After that, equal volume of both systems was mixed and vortexed at 35 Hz for 3 min until the transparent nanoemulsion was produced. Formation of a transparent nanoemulsion was judged by measuring the globule size of the nanoemulsion at 22° C. (Shankar R, Tiwari V, Mishra C P, Singh C K, Sharma D, Jaiswal S. Formulation and evaluation of nanoemulsion for solubility enhancement of ketoconazole. Int J Res Pharm Nanosci 2015; 4(6):365-78, incorporated by reference herein in its entirety).

| Formulation code | Oleic acid | Tween 80 | PEG 200 | Globule size (nm) | Polydispersity index | Zeta potential (mV) |
|---|---|---|---|---|---|---|
| 1 | 15.0 | 50.0 | 35.0 | 157.7 | 0.36 | 53.0 |
| 2 | 15.0 | 45.0 | 40.0 | 152.7 | 0.28 | 53.6 |
| 3 | 10.0 | 50.0 | 40.0 | 92.5 | 0.58 | 49.1 |
| 4 | 14.1667 | 49.1667 | 36.6667 | 135.1 | 0.42 | 55.9 |
| 5 | 14.1667 | 46.6667 | 39.1667 | 146.6 | 0.42 | 59.5 |
| 6 | 11.6667 | 49.1667 | 39.1667 | 93.4 | 0.45 | 52.7 |
| 7 | 15.0 | 47.5 | 37.5 | 141.1 | 0.42 | 61.0 |
| 8 | 12.5 | 50.0 | 37.5 | 102.8 | 0.43 | 49.2 |
| 9 | 12.5 | 47.5 | 40.0 | 108.5 | 0.43 | 53.7 |
| 10 | 13.3333 | 48.3333 | 38.3333 | 135.4 | 0.48 | 55.8 |

Example 2: Evaluation of the Nanoemulsion Formulations

The SNEDS were inspected visually for its clarity and its ability to be emulsified spontaneously upon mixing of its components. Briefly, a specific weight (50 mg) of the SNEDS formulation was placed into 100 mL of distilled water and observed visually for the emulsification ability. Visual observations were made immediately after dilution for spontaneous emulsification, transparency, phase separation, and drug precipitation.

Aliquots of 20 mL distilled water containing 100 mg of each formulation were used to determine the globule size and zeta potential by dynamic light scattering using a by dynamic light scattering with a Malvern Zetasizer Nano ZSP, Malvern Panalytical Ltd. (Grovewood Table 1. Composition and assessment of SNEDS formulations according to the mixture design. Road, United Kingdom). The experiment was performed in triplicate. The globule size, polydispersity index (PDI), and the zeta-potential for each formulation are provided in Table 1. The zeta potential was high in all the formulations suggesting a high degree of electrostatic repulsion between NaOCl and CHX and excellent stability.

The obtained data for the globule size and zeta potential of the prepared SNEDS were analyzed and the independent and dependent variable were related using regression equation and desirability function approach to achieve a formulation with minimum globule size and maximum zeta potential.

Figure 2:
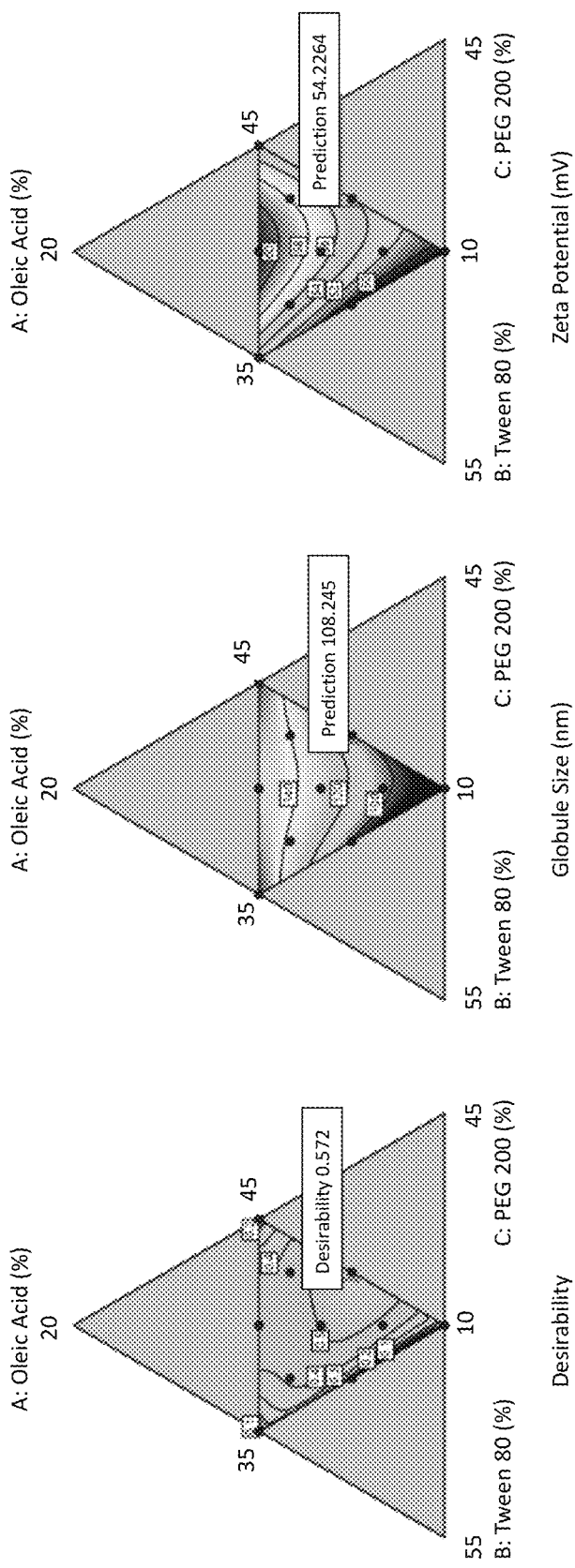
FIG. 2 is a calculation based on the desirability, zeta potential, and globule size, to determine a combination of oil, surfactant, and co-surfactant, according to certain embodiments.

After analyzing mixtures globule size and zeta potential, a multiple response optimization was done using (Mixture designs—XLSTAT by Addinsoft). This procedure helps determine the maximum desirability function with the combination of experimental factors, globule size and Zeta potential. The combination of factor levels which maximize the desirability function over the indicated region is presented in (Table 2) (FIG. 2). It also shows the combination of the factors at which that preferred value is achieved=0.571609 with globule size=108.262 and zeta potential=54.2279. The SNEDS was prepared according this formula.

TABLE 2

A SNEDS embodiment.

| Factor | Low | High | Optimum |
|---|---|---|---|
| Oleic acid | 10.0 | 15.0 | 12.3641 |
| Tween 80 | 45.0 | 50.0 | 47.7465 |
| PEG 200 | 35.0 | 45.0 | 39.8895 |

Example 3: Characterization and Evaluation of Prepared CHX—NaOCl Nanoemulsion

An Agilent 6320 liquid chromatography-ion trap mass spectrometer (LC-IT-MS) was used for the characterization of presence of 4-Chloroaniline of molecular mass 127.57.

The MS system was connected to an HPLC-Agilent 1200 system equipped with an auto sampler, a quaternary pump, and a column compartment (Palo Alto, CA, USA). The system was equipped with ChemStation software (Rev. B.01.03 SR2(204)). The IT-MS was controlled using 6300 series trap control version 6.2 Build No. 62.24 (Bruker Daltonik GmbH), and the general MS adjustments were: capillary voltage, 4200 V; nebulizer, 37 psi; drying gas, 12 L/min; desolvation temperature, 330° C.; ion charge control (ICC) smart target, 200,000; and max accumulation time, 200 millisecond (ms). The MS scan range was 50-550 m/z at positive ion mode. Mobile system: isocratic elution with a mobile system composed of 52% acetonitrile and 48% water containing 0.1% formic acid, at flow rate of 0.5 mL/min, injection volume, 10 µL.

TABLE 3

Mass spectra of Sample.

| Sample | m/z [M + H] |
|---|---|
| CHX-NaOCl nanoemulsion | 413 |

Figure 3A:
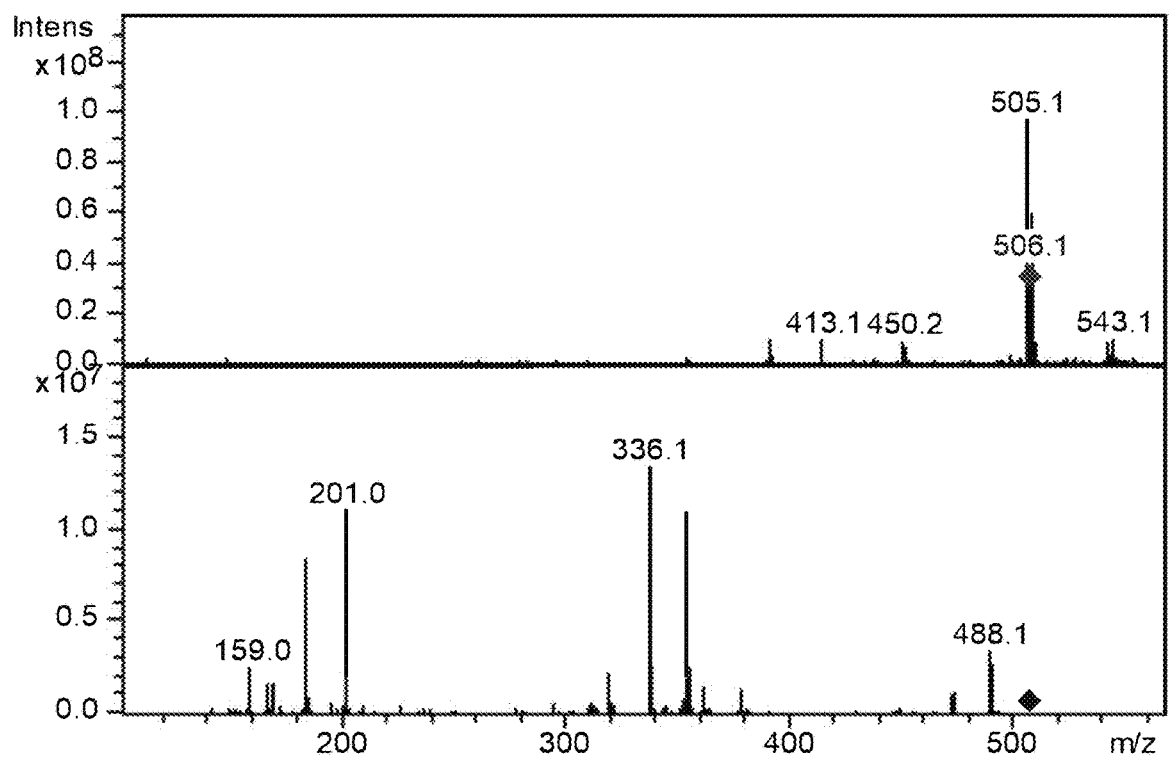
FIG. 3A-B shows a mass spectrum of a CHX—NaOCl nanoemulsion, with 3B as a zoomed in view, according to certain embodiments.
Figure 3B:
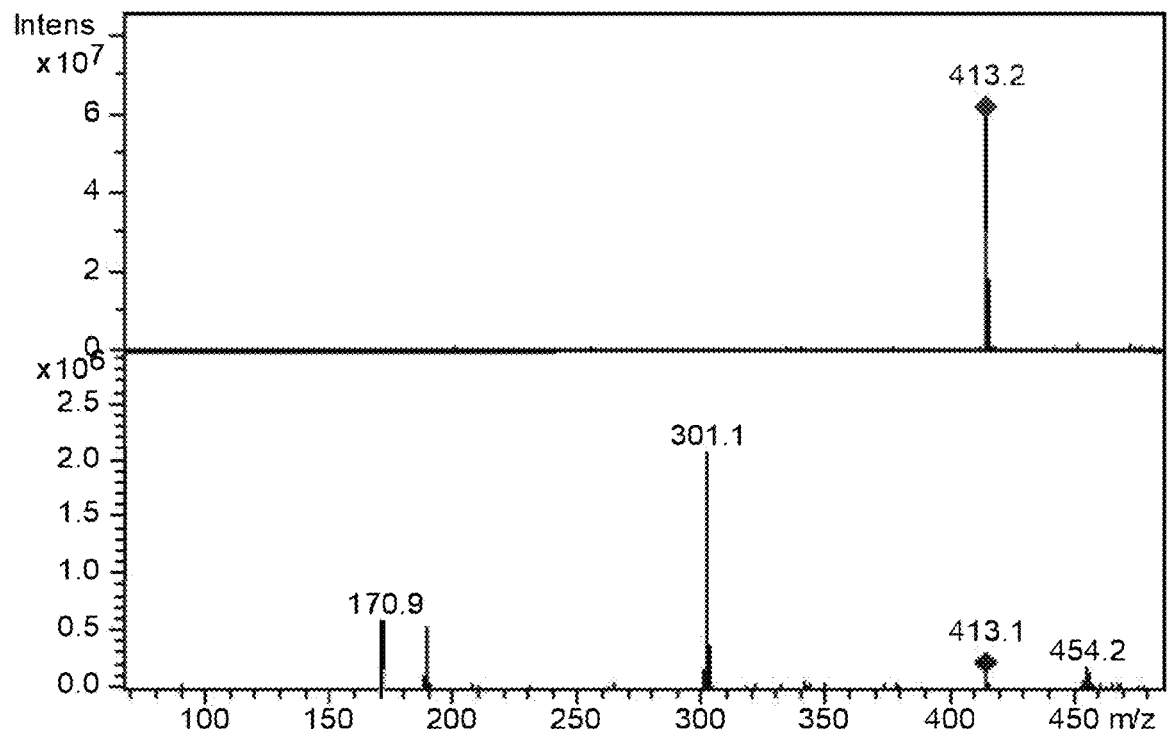

The CHX—NaOCl nanoemulsion (FIG. 3A-B) does not have 4-Chloroaniline of molecular mass 127.57.

To determine phase separation, 3 mL of the CHX—NaOCl nanoemulsion mix were stored for 48 hours at ambient temperature and observed for phase separation. Then 1 mL samples of the CHX—NaOCl nanoemulsion were diluted to 5 mL with distilled water at 25° C. and stored for a period of 24 hours and observed for phase separation. Visual observations showed the sample to be transparent without phase separation or drug precipitation.

Example 4: Tissue Dissolving Capacity

Dental pulp from teeth extracted for orthodontic reasons or impacted third molars was used. After extraction, the teeth were kept at −20° C. until required. Then, the teeth were maintained at room temperature, further to which longitudinal grooves were cut on the proximal surface with a diamond bur to split the teeth into two halves. Further, the dental pulp was removed and washed with distilled water and divided into sections, each weighing approximately 25 mg. Samples were categorized into four groups. Group 1, 2, and 3 each contained eight samples, while group 4 (control group) contained four samples. Each sample was weighed on a digital scale before the experiment and transferred to a coded experiment tube. After preparation of samples, 2 ml of an experiment solution, namely, 1% CHX, 2.5% NaOCl, NaOCl—CHX nanoemulsion, and normal saline, were poured on the dental pulp sample in the coded experiment tube with a syringe. The sample was further placed on a vibrator for 2 minutes. After 2 minutes, the experiment solution was extracted by syringe from the experiment tube. Then 2 ml fresh solution was further added to the sample and placed on the vibrator for two minutes. This process was performed ten times for each sample. By this method, each sample would have been contacted with a new experiment solution for 20 minutes. After 20 minutes, all the experiment solution was extracted by syringe from the tube, and the sample was dried. The weight of the dry pulp sample was measured by the same digital scale and recorded. The weight loss after drying was calculated by the following equation.

$$\text{Percentage weight loss} = (\text{Weight(final)} * 100)/\text{Weight(initial)} \quad (1)$$

Where weight(initial) refers to the weight of the tissue sample before contact with the experiment solution, and weight (final) refers to the weight of the tissue sample after contact with the experiment solution.

Example 5: Biocompatibility Tests

L929 fibroblasts, primary fibroblast extracted from human granulation tissues, and human osteoblast-like cells (Saos-2) were exposed to 1% CHX, 2.5% NaOCl, and CHX—NaOCl nanoemulsion. Cell viability was assessed by methyl-thiazole tetrazolium (MTT) and neutral red (NR) assays.

Example 6: Antibacterial Activity on *E. faecalis* Biofilm

Preparation of Tooth Samples

The sample size calculation was conducted using Gpower (version 3.1). Based on Cohen's conventions, a significant size effect (f=0.4) was assumed between different means (5 groups) with a 5% two-sided type I error and a power of 80%. A total sample size of 80 was required (N=16 for each group). Eighty extracted caries-free single-rooted teeth were used in the study. The teeth were kept in 0.1% NaOCl solution before use. A root dentin block with a length of 6 mm was horizontally sectioned from each tooth at 1 mm below the cementoenamel junction. The inner diameter of the dentin blocks of each sample was standardized using a Gates Glidden size three drill. The teeth and the dentin blocks will be kept in tap water during all procedures to avoid dehydration. The smear layer will be removed by treatment in an ultrasonic bath in 17% EDTA (4 min) and 5.25% NaOCl (4 min). The external surfaces of the samples were coated with nail varnish, and the blocks were sterilized by autoclaving for 36 min at 121° C. Sterilization efficacy will be checked by randomly selecting five dentin disks and incubating them in the BHI broth for 24 hours.

*E. faecalis* Biofilm Generation and Specimen Contamination

Pure culture of *E. faecalis* (ATCC 29212) cultivated in brain heart infusion (BHI) broth anaerobically for 24 hours at 37° C. was used to contaminate the specimens. The optical density of the bacterial suspension was adjusted spectrophotometrically to approximately $1.5 \times 10^7$ colony forming units (CFU)/ml (concentration equivalent to 0.5 in the McFarland standard). To contaminate the 64 dentin blocks (16 specimens were not contaminated to act as negative control), an inoculum of pure suspension of 0.05 *E. faecalis* into 600 µl of tryptic soy broth was suspended into the prepared sterilized in 12-well tissue culture plate. The blocks were then incubated anaerobically at 37° C. for three weeks with a change of the growth medium once every three days to provide a constant microbial growth rate during the incubation period. Gram staining and microscopic assessment of colony morphology were used to confirm the monoculture of *E. faecalis*. After an incubation period, the specimens were aseptically removed from the wells and gently rinsed with sterile phosphate-buffered saline for 1 minute.

Irrigation of the Dentin Blocks

Sixty-four incubated dentine blocks were randomly divided into four groups containing 16 specimens each. The irrigants were tested with 2.5% NaOCl, 1% CHX, CHX—NaOCl nanoemulsion, and normal saline "positive control" and were applied to the canal lumen for 3 minutes and then washed with normal saline and dried with a sterile paper point. The medicated blocks were incubated anaerobically at 37° C. in the air for seven days.

Dentin Sampling

Dentin chips were harvested from the dentin block by circumferential removal using a low-speed handpiece with a Gates Glidden size four (4) drill. The dentin chips obtained were collected in Eppendorf tubes containing 0.5 mL of saline to obtain a suspension. The suspension was then homogenized by vigorous vortexing to release the adhered bacteria and left for 5 minutes to allow for sedimentation of the dentin chips. The supernatant containing the bacterial suspension was then used for microbiological analysis to determine the number of colony-forming units (CFUs).

The nanoemulsion of the present disclosure uses a combination of NaOCl and CHX, which when used in defined ratios along with SNEDS (oil, surfactant, and co-surfactant), demonstrates excellent tissue dissolving ability, biocompatibility, and imparts antimicrobial property. Also, the low globule size of the nanoemulsion and the high zeta-potential value suggest a high degree of stability and minimal interaction between the two irrigants. This can be confirmed by the lack of PCA, as a result, drawbacks such as cytotoxicity and dentin staining can be overcome with the nanoemulsion of the present disclosure. The nanoemulsion of the present disclosure possesses unique properties of NaOCl and CHX without affecting each other, thereby maximizing the antibacterial efficacy, and tissue dissolving capacity as well, with low cytotoxicity.

Example 7: Antibacterial Activity on Bacteria and Fungus

The antimicrobial activity of the tested irrigant (5.25% NaOCl solution, NaOCl nanoemulsion, 2% CHX solution, 2% CHX nanoemulsion, 1% CHX nanoemulsion, CHX—NaOCl nanoemulsion) was done against standard strains of two bacteria and one fungus. These strains included Gram positive bacteria: *Enterococcus faecalis* ATCC 29212 and Gram negative bacteria: *Escherichia coli* ATCC 35218 and fungus: *Candida albicans* ATCC 76615.

Preliminary screening of the antibacterial and antifungal activities was conducted using agar diffusion technique, as described previously in Clinical and Laboratory Standards Institute. Methods for Dilution Antimicrobial Susceptibility Tests for Bacteria That Grow Aerobically; Approved Standard M7-A7; Wayne, PA, USA, 2006; Volume 26, incorporated by reference herein in its entirety. Briefly, Petri dishes (150 mm) were filled with 50-mL Muller-Hinton agar containing 1 mL bacterial culture ($1 \times 10^6$ CFU/mL). The strains were inoculated separately. Seven holes (4 mm in diameter) were made in the seeded agar plates. The holes were then filled with 50-µL of the tested irrigant, and normal saline was used as negative control. Dishes were then incubated for 24 h at 37° C.). Inhibitory activity was defined as the absence of bacterial growth in the area surrounding the holes. The inhibition zone was measured using a caliper. The experiment was done in triplicate.

All tested irrigants showed zone of inhibition indicating antimicrobial activity except the negative control group. The zones of inhibition of the CHX—NaOCl nanoemulsion mixture group were significantly larger than the other groups. The maximum zones of inhibition were 26.8 mm±1.8 in the CHX—NaOCl nanoemulsion mixture group.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A nanoemulsion, consisting of:
   a self-nanoemulsifying delivery system (SNEDS), wherein the SNEDS consists of:
      about 12 wt. % of an oil;
      about 48 wt. % of a surfactant; and
      about 40 wt. % of a cosurfactant, based on a total weight of the SNEDS;
   sodium hypochlorite (NaOCl) in a 1:1 by volume ratio with the SNEDS; and
   chlorhexidine (CHX) in a 1:1 by volume ratio with the SNEDS;
   wherein no parachloroaniline is present in the nanoemulsion after 1 hour at room temperature,
   wherein the nanoemulsion has a globule size of about 108 nm, and
   wherein the nanoemulsion has a zeta potential of about 54 mV.

2. The nanoemulsion of claim 1, wherein:
   the oil is at least one selected from the group consisting of isopropyl myristate, olive oil, sunflower oil, soyabean oil, safflower oil, coconut oil, ethyl oleate, oleic acid, glyceryl dicaprate, glycerol caprylate caprate, and glyceryl monocaprylate.

3. The nanoemulsion of claim 1, wherein:
   the surfactant is at least one selected from the group consisting of polyoxyethylene (20) sorbitan monooleate, polyethoxylated castor oil, polyoxyethylene (20) sorbitan monolaurate, poloxamer 188, and lauroyl polyoxyl-32 glyceride.

4. The nanoemulsion of claim 1, wherein:
   the cosurfactant is at least one selected from the group consisting of oleoyl polyoxyl-6 glycerides, polyglyceryl-3 dioleate, ethanol, polyethylene glycol (PEG) 200, carbitol, and ethylene glycol.

5. The nanoemulsion of claim 1, wherein:
   the oil is oleic acid.

6. The nanoemulsion of claim 1, wherein:
   the surfactant is polyoxyethylene (20) sorbitan monooleate.

7. The nanoemulsion of claim 1, wherein:
   the cosurfactant is polyethylene glycol 200.

8. The nanoemulsion of claim 1, wherein:
   the CHX is dispersed within a first group of SNEDS particles;
   the NaOCl is dispersed within a second group of SNEDS particles; and
   the NaOCl and CHX do not have physical contact.

9. The nanoemulsion of claim 1, wherein:
   at least 95% of human cells are viable after exposure to the nanoemulsion.

10. A method of making the nanoemulsion of claim 1, comprising:
    mixing the oil, surfactant, and cosurfactant to form a mixture;
    combining the mixture with NaOCl or CHX to form a NaOCl nanoemulsion solution or a CHX nanoemulsion solution, respectively, and vortexing the solutions for at least 10 seconds; and
    combining the NaOCl nanoemulsion solution and CHX nanoemulsion solution and vortexing for at least 2 minutes to form the nanoemulsion.

11. The nanoemulsion of claim 1, wherein the nanoemulsion is an irrigant formulation for reducing a bacterial proliferation in a root canal of a patient:
    wherein the reduction of the bacterial proliferation is compared to a bacterial proliferation of the otherwise same root canal when treated in the otherwise same manner except without administering the nanoemulsion or derivative thereof; or
    wherein the reduction of the bacterial proliferation is compared to a bacterial proliferation of the otherwise same root canal when treated with NaOCl or CHX with no SNEDS present.

12. A method of irrigating a root canal during an endodontic procedure, comprising:
    providing access to the root canal of a tooth; and
    introducing the nanoemulsion of claim 1 to the root canal.

13. The method of claim 12, further comprising making the nanoemulsion immediately prior to the irrigating,
    wherein the SNEDS, the NaOCl, and the CHX are provided in three separate solutions, and
    wherein the nanoemulsion is made by a method comprising:
    combining the SNEDS with the NaOCl or the CHX to form a NaOCl nanoemulsion solution or a CHX nanoemulsion solution, respectively, and vortexing the solutions for at least seconds; and
    combining the NaOCl nanoemulsion solution and CHX nanoemulsion solution and vortexing for at least 2 minutes to form the nanoemulsion.

* * * * *